United States Patent [19]

West et al.

[11] 4,455,086
[45] Jun. 19, 1984

[54] OPTICAL TEST APPARATUS FOR EXAMINING AN OBJECT

[75] Inventors: Robert N. West, Chislehurst; Andrew J. Barker, Orpington, both of England

[73] Assignee: Sira Institute Limited, England

[21] Appl. No.: 347,132

[22] Filed: Feb. 9, 1982

[51] Int. Cl.³ .............................................. G01N 21/00
[52] U.S. Cl. .................................. 356/237; 250/563; 250/572; 250/237 G; 356/239
[58] Field of Search ............... 356/237, 239, 371, 431; 250/563, 572, 237 G

[56] References Cited

U.S. PATENT DOCUMENTS

| 2,867,149 | 1/1959 | Goddard | 356/371 |
| 3,185,022 | 5/1965 | Holeman | 356/371 X |
| 3,788,750 | 1/1974 | Maltby, Jr. et al. | 356/239 |

FOREIGN PATENT DOCUMENTS 1574423  9/1980  United Kingdom ............... 356/431

OTHER PUBLICATIONS

Sira, "Lasers in the Glass Industry", *Glass*, vol. 51, No. 9, pp. 309-312, Sep. 1974.

*Primary Examiner*—William L. Sikes
*Assistant Examiner*—Matthew W. Koren
*Attorney, Agent, or Firm*—Neil F. Markva

[57] ABSTRACT

Test apparatus and method for testing for faults in, for example, transparent sheet material in which two parallel beams of light separated by a distance "w" are passed through a grating having, for example, light transmitting and absorbing areas separated by a distance "w", so that as the two beams are scanned across the object and the grating the light output through the grating is generally constant. If, however, there are faults which displace one beam with respect to the other, then the spacing between the beams will change so the light output will vary from the norm. Furthermore, if there is a fault which would cause attenuation of the two beams, then the light output will again vary from the norm.

25 Claims, 13 Drawing Figures

OPTICAL TEST APPARATUS FOR EXAMINING AN OBJECT

The present invention relates to test apparatus for examining an object such as a transparent material for faults.

SUMMARY OF THE INVENTION

According to one aspect, the invention comprises optical test apparatus for examining an object comprising means for providing two beams of radiation, grating means for each beam, means for scanning each beam across the object and across its respective grating means so that each beam is influenced by the object and by its respective grating. The grating means comprises first and second alternately arranged areas which influence the radiation in different ways, successive areas being of substantially the same width in the direction of scan. The beams are displaced relative to one another and/or the grating means are displaced relative to one another by a total distance in the direction of scan equal to an odd number of widths so that, at all times during the scan, in the absence of faults in said object, one of the beams is being influenced by an area of the first type and the other of the beams is being influenced by an area of the second type. Collector means collect the beams of radiation after they have been influenced by the grating means and the object.

The alternate areas of the grating means may comprise radiation absorbing and radiation transmitting areas or radiation absorbing and radiation reflecting areas or radiation transmitting and radiation reflecting areas.

Effectively the beams and gratings are arranged so that so long as the object under test does not divert one beam relative to the other then the radiation collected by the radiation collector will be generally constant. The reason for this is that since the beams and/or the grating means are normally displaced relative to one another by a total distance in the direction of scan equal to an odd number of widths, as one beam enters a first one of the alternate areas then the second beam will enter a second one of the alternate areas. If, however, the object under test influences the two beams so as to vary the distance in the direction of scan between them or by attenuating the beams, for example because of faults in the object, then this will result in a change of radiation received by the radiation collector.

Thus the faults may be detected by considering the radiation collected by the collector. It will, however, be understood that what might be considered to be a fault in one application, may not be considered so in another application, but for the sake of clarity these differences from norm will be referred to hereafter as faults.

The respective grating means for each beam may be provided by a single grating or by two gratings in phase with one another, or by two gratings out of phase with another for example, by a distance equalling the width.

The source of radiation preferably comprises a laser.

The invention also provides a method of examining an object comprising scanning two beams of radiation across the object and across respective grating means so that each beam is influenced by the object and by its respective grating means. Each grating means comprises first and second alternately arranged areas which influence the radiation in different ways. Successive areas are substantially the same width in the direction of scan. The beams are being displaced relative to one another and/or the grating means are displaced relative to one another by a total distance in the direction of scan equal to an odd number of widths so that, at all times during the scan, in the absence of faults in said object, one of the beams is being influenced by an area of the first type and the other of the beams is being influenced by an area of the second type. The radiation influenced by both the grating means and the object is then collected and analyzed.

By analyzing the radiation collected, it is possible to detect faults in the object and in some circumstances identify them.

The object may comprise, for example, a transparent material in which case the radiation may be passed through the material before passing to the grating means or may comprise reflective material in which case the radiation may be reflected from the material before being passed to the grating means.

Such optical test apparatus may be used in manufacturing processes to inspect material and to reject, for example, faulty material.

The collector means may take various forms. If it is convenient, the radiation passing through the grating may be collected from behind the grating means. Alternatively, reflective, diffuse or retro-reflective means may be provided behind the grating means to reflect radiation back through the grating means and means may be provided to separate the incident radiation from the reflective radiation by a suitable beam splitter. Because of the diffuse nature of the radiation beam reflected back through the grating means, the grating means has no overall effect apart from minor attenuative effect.

Throughout the specification the term "radiation" is intended to not only include visible wavelengths which will be referred to as light but also ultraviolet, infra-red and other wavelengths. The term "optics" and "optical" should be similarly interpreted.

BRIEF DESCRIPTION OF THE DRAWINGS

Various embodiments of the invention will now be described by way of example only and with reference to the accompanying drawings in which.

DESCRIPTION OF PREFERRED EMBODIMENTS

Figure 3:
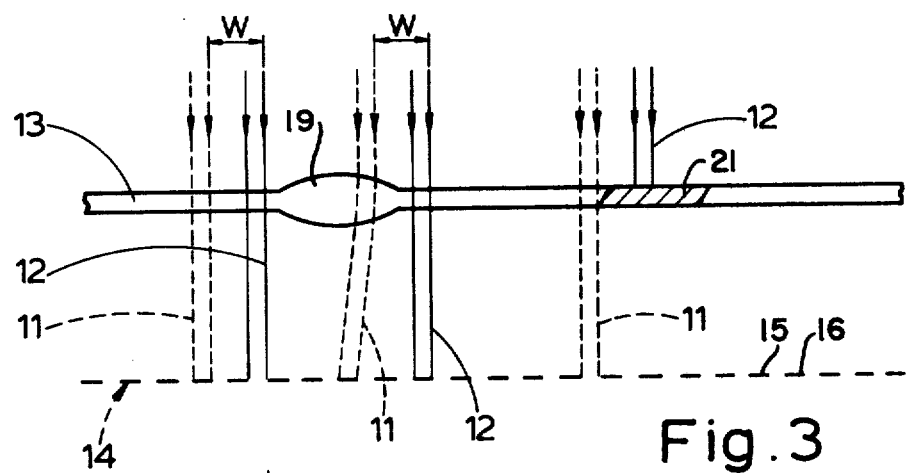
FIG. 3 is a diagram illustrating the principle of the invention.
Figure 4:
FIG. 4 is a diagram of the output signal produced by the apparatus, FIGS. 3 and 4 being vertically aligned.

The invention will be most readily understood with reference to FIGS. 3 and 4. In FIG. 3 it will be appreciated that two generally parallel beams 11, 12 of radiation are scanned across an object under examination in the form of a transparent sheet 13. Various faults may be present in the sheet 13 such as bubbles, surface damage, and absorption defects, the faults being exaggerated in FIG. 3 so as to be clear. Mounted below the sheet 13 is a pattern in the form of a grating 14. The grating 14 comprises a regular linear grating of alternate radiation transmitting areas 15 and radiation absorbing areas 16 of the same width "w" and at least at the grating 14 the two beams 11, 12 are spaced apart by the distance "w".

At the extreme left side of FIG. 3, the beams 11, 12 pass through a normal part of the sheet 13 and as they are scanned from left to right the two beams 11, 12 pass alternately through the light transmitting areas 15 and the light absorbing areas 16 of the grating 14. The two beams will have a cross section comprising a portion of the distance "w" (for example, the beams might have a cross section in the range (w/10) to (w/2) and preferably (w/2) and so as one beam passes into the light transmitting area 16 the other beam will similarly be passing into a light absorbing area and the net amount of radiation passed through the grating will remain substantially constant. Thus the light collected by the light collector or detector (not shown) is substantially constant and this produces a generally constant output signal as is indicated in FIG. 4 below the extreme left portion of the sheet 13.

Considering now the fault 19 shown in FIG. 3, this distortion will produce a change in the path of the beams 11, 12 as they pass through the fault. As the first beam reaches the fault 19, it will be distorted away from its original position and because the two beams are not now spaced by distance "w" light from both beams 11, 12 or from neither beam 11, 12 will pass through the grating 14 and fall on the light collector or detector. During the passage of the two beams 11, 12 across the fault 19 they will generally not be spaced by the distance "w" (or by an odd multiple thereof) and thus either both beams will pass through the grating or neither will pass through the grating at least at some time. The distortion fault 19 will therefore be readily indicated by observing and measuring the variation of output of the light collector or detector as is indicated in the middle of FIG. 4.

A second type of fault often encountered is a light absorbing area indicated at 21 in FIG. 3 and in this area 21 light from neither beam will pass through the sheet 13 or at least will be attenuated and the output of the light detector will fall from its normal value. This is indicated on the right hand side of FIG. 4.

At this stage it will be understood that according to the principle of the invention the two beams should be spaced apart with respect to their grating means by the width of one of the light absorbing or transmitting areas 15 and 16 so that at all times during the scan, in the absence of faults in the sheet, one of the beams is being absorbed and the other is being transmitted by their respective gratings.

Figure 5:
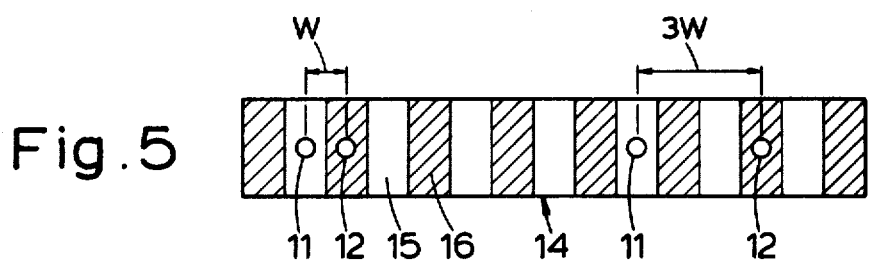
FIGS. 5 to 9 show diagrammatically various relative arrangements of beam and grating means.

The arrangement so far described is shown with reference to FIG. 5 which shows the grating 14 and the two beams 11, 12 spaced on the left hand side of FIG. 5 by the distance "w" and in an alternative arrangement at the right hand side by a distance equal to 3w.

Figure 6:
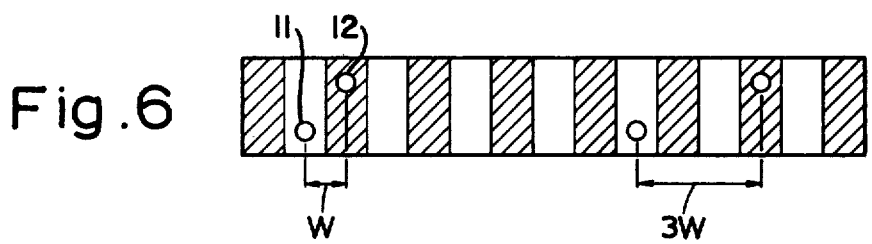

Other arrangements are clearly possible. In FIG. 6 it will be seen that two cases similar to those in FIG. 5 are shown except that the two beams 11, 12 are displaced at right angles to the line of scan. There are certain advantages in carrying out the method in this way.

Figure 7:
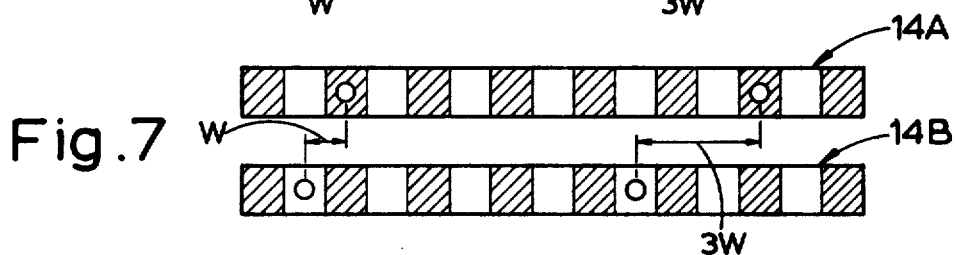

The arrangement in FIG. 7 is the same as in FIG. 6 except that the grating has been split into two portions 14A and 14B which are displaced at right angles to the line of scan.

Clearly the two portions of the grating can be displaced by as great a distance as is required.

Figure 8:
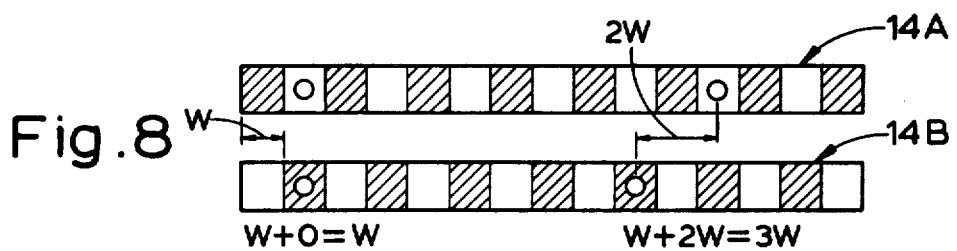

In the arrangements described so far and, in particular in FIG. 7, it will be understood that the two grating portions 14A, 14B are maintained so that the distance between any two corresponding areas in the direction of scan is zero. However, it is not necessary to maintain this relationship. For example in FIG. 8 one grating portion 14A has been displaced in the direction of scan with respect to the other grating portion 14B by the width w. In these circumstances it is then necessary to displace the two beams 11, 12 by the distance w so as to maintain the same relevant relationship between the two beams and the grating portions. In practice, of course, the two grating portions may be displaced relative to one another by any odd number of widths. In other words, one width, three widths, five widths and so on.

Figure 9:
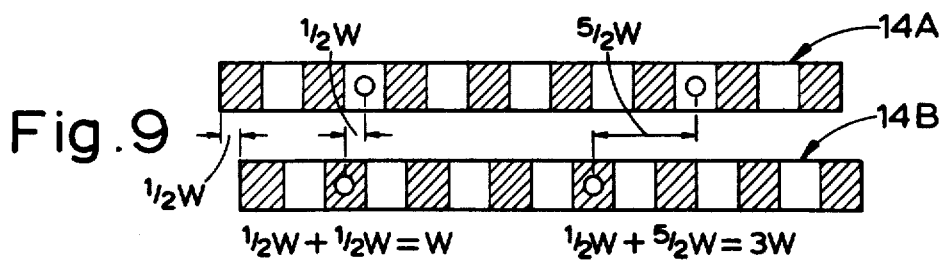

FIG. 9 shows another possible case in which the two grating portions have been displaced by half of a width and the two beams 11, 12 have also been displaced by half a width so as to again maintain the same relative relationship between the grating and the beams. The total displacement between the two grating portions and the two beams must be equal to the width w or an odd number of widths, $(2n+1)w$ where n is any number. Thus in a further arrangement, not shown, one might displace the two grating portions by some part of a width w and the two beams must be displaced by a distance which meets the above relationship, that is, that total relative displacement of the two grating portions and the two beams must be an odd number of widths.

Figure 2:
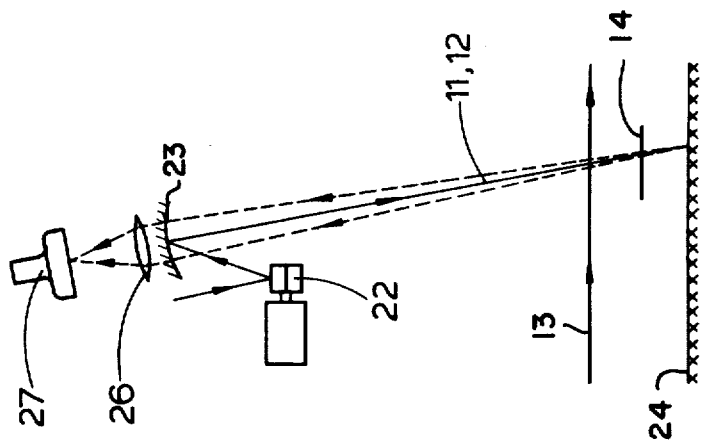
FIG. 2 is a side view of the apparatus of FIG. 1.
Figure 1:
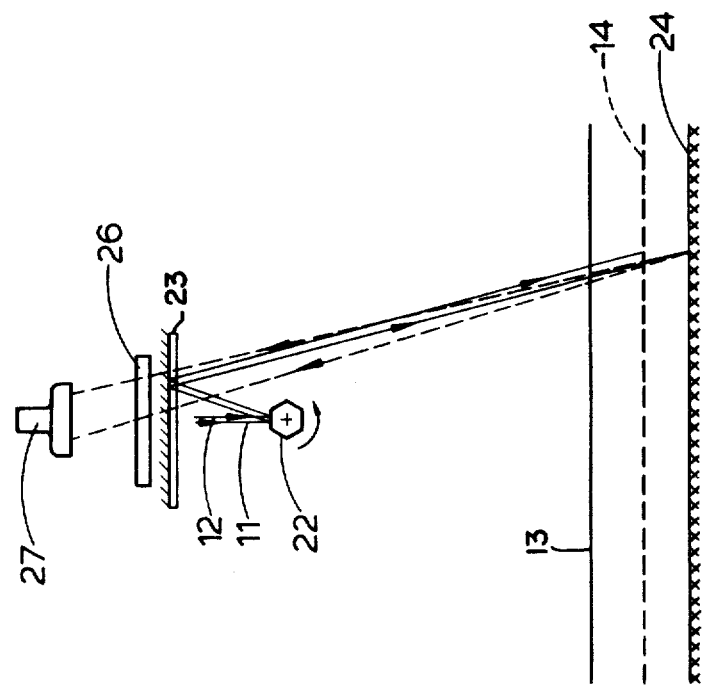
FIG. 1 shows a front diagrammatic view of an apparatus according to the invention.

FIGS. 1 and 2 illustrate the preferred apparatus of the invention which corresponds to FIGS. 3, 4 and 5. The apparatus is particularly adapted to examine for faults in a strip or sheet of transparent material being produced by a manufacturing process.

The apparatus comprises a laser (not shown) for producing a beam which is split by a beam splitter to form the two essentially parallel beams 11, 12.

The two beams 11, 12 are reflected from a mirror drum scanner 22 onto a cylindrical mirror/beam splitter 23. The cylindrical mirror 23 reflects the light from the mirror drum scanner 22 so as to scan the beams 11, 12 transversely across the sheet 13 under inspection.

In FIG. 1 the length of the strip or sheet 13 extends out of the plane of the paper and the sheet moves in a direction along its length. The mirror drum scanner 22 thus causes the light beams 11, 12 to scan from one side of the sheet 13 to the other as shown in FIG. 1.

The light transmitted by the sheet 13 is passed through the linear grating 14 on to a retroreflective layer 24 which extends behind the grating 14. The light incident on the retroreflective layer 24 is retroreflected (that is is reflected back along the incident path with slight scatter) and passes back to the grating 14. However, because of the scattering effect of the retroreflective sheet the light passes through the grating 14 without any similar effect of that of the incident beam, the grating merely slightly attenuating the reflected light. The reflected light is passed back to the cylindrical mirror/beam splitter 23, through a cylindrical lens 26 to be focused on to a photomultiplier 27.

The grating 14 is arranged so that its alternate light transmitting areas and light absorbing areas 15 and 16 extend out of the plane of the paper in FIG. 1 and parallel to the plane of FIG. 2. The use of a cylindrical mirror 23 allows for focusing of the light beams in the plane of FIG. 1 and separate focusing in the the plane of FIG. 2 so that the surface inspected sheet 13 and facet of mirror drum 22 are at conjugate points in the plane of FIG. 2.

The mode of operation of the apparatus of FIGS. 1 and 2 will be readily apparent after consideration of FIGS. 3 and 4. By rotating the mirror drum scanner 22, the beams 11, 12 are traversed across the inspected sheet 13 in the plane of FIG. 1 while the inspected sheet 13 moves at right angles to the plane of FIG. 1 and the signal produced at the photomultiplier 27 by the light received is generally of the form shown in FIG. 4.

By focusing the light at the photomultiplier 27 by means of the cylindrical lens 26, the effect of ambient light can be much reduced. In place of a retroreflective material in the arrangement of FIGS. 1 and 2, a matt white surface can be used although of course not so much light is reflected.

In alternative arrangements, in place of a planar retroreflective layer 24 and planar grating 14 there may be provided a curved retroreflective layer and a curved grating, the center of curvature of the layer and grating being at the mirror drum scanner 22 (taking into account the folding of the optical axis). The reason for the curving of the retroreflective layer and the grating is that, in FIG. 1, as the light beams are scanned across the linear grating and linear retroreflective layer, by virtue of the different angle of incidence, the distance between the beams "w" when measured in the plane of the grating will increase and thus the width of the light transmitting and absorbing areas of the grating must be varied. With a curved grating and a curved retroreflective layer this is unnecessary as the angle at which the two beams reach the grating is always normal to the grating. Furthermore, the beams are in focus accurately at all points along the scan when they meet the grating.

In another arrangement, to overcome the problem of the distance between the beams when measured in the plane of the grating increasing as the beams are scanned across the grating, one may arrange for the two beams to be slightly non-parallel and to be directed so as to converge so that, in the absence of the retroreflective material, they would meet at a point behind the retroreflective material. The point to which they converge should be the same distance from the grating as the distance between the grating and the mirror drum scanner 22. The effect of the two beams converging as they move away from the mirror drums compensates for the increase in distance between the two beams as they scan across the grating almost exactly so that the width between the beams in the plane of the grating remains almost constant as they are scanned across the planar grating.

In another arrangement, the grating, which may be curved may be combined with a cylindrical mirror in place of the retroreflective layer to reflect the beams back in the incident direction. The cylindrical mirror may in this instance form a grating by including areas of non reflective material corresponding to the absorbing area 16 and the mirror may be constructed of a flexible material such as glass or plastics which is flexed about two supports as disclosed in our U.S. Pat. No. 3,814,945.

A greater light intensity is achieved utilizing this arrangement but it is more difficult to set up.

In another arrangement, the radiation which is passed through the grating 14 is not reflected back along the same path by a retroreflective layer or by a mirror but is collected by suitable optical components from the side of the grating 14 opposite the sheet 13. This may be achieved by providing a cylindrical lens, the longitudinal axis of which is transverse to the plane of the scanned light and the width of which enables all of the light from the grating 14 to be collected from one end of the scan to the other. The cylindrical lens focuses the light via a second cylindrical lens having a longitudinal axis at right angles to the first cylindrical lens on to a photomultiplier. In this arrangement beams of radiation only pass through the grating once.

It may be arranged that the two beams are brought to a focus at the object under test since in this way even quite small defects in the object will displace the beams. It may thus be arranged that the beams are each brought to a focus at the object and are defocused to the extent that their cross section is (w/2) at the grating.

An alternative arrangement will be described with respect to FIGS. 10 to 13 which overcomes a potential problem of matching the characteristics of the two beams. It sometimes becomes difficult to match exactly the characteristics such as intensity of the two beams. If they are of different intensities, as the light detector changes from detecting one beam to the other as the beams scan across the grating then the intensity of the light detected will vary and a false reading may be produced. It is therefore desirable that the two beams 11, 12 which are produced by a beam splitter from a single beam should be produced by a beam splitter positioned as the last optical item before the beam strikes the sheet 13.

Figures 10, 11:
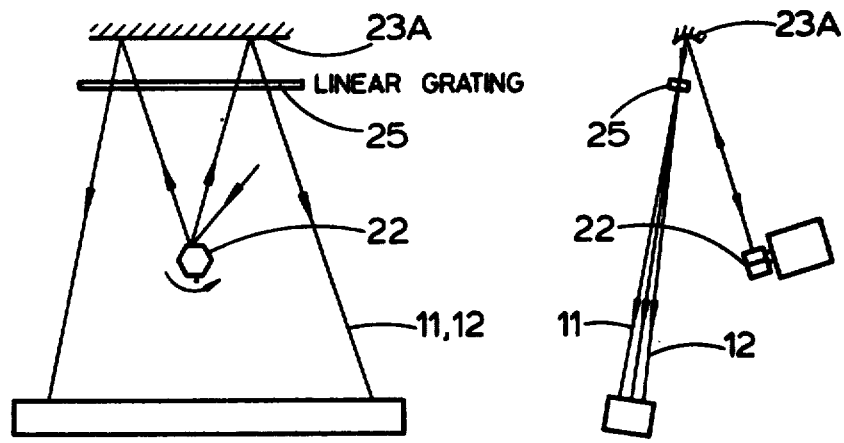
FIG. 10 shows a front diagrammatic view of an alternative apparatus according to the invention.
FIG. 11 is a side view of the apparatus of FIG. 10.
Figure 12:
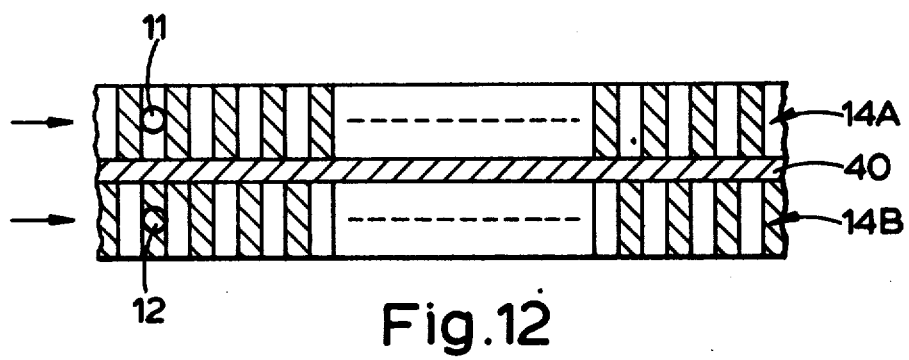
FIG. 12 shows diagrammatically the relative arrangement of beams and grating means for use with the arrangement of FIGS. 10 and 11.

In the arrangement of FIG. 10 a beam splitter 25 is provided separately from the mirror 23A and below the mirror so that the beam is not split until just before passing to the sheet 13. The beam splitter 25 comprises a linear grating in which the grating lines are along the length of the grating. The spacing of the grating lines is chosen to produce diffraction of the incident single laser beam so that two first order beams are formed. There will also be formed a zero order diffraction beam which is eliminated in practice by a matt black strip 40 (see FIG. 12) between the two gratings 14a, 14b, and second and subsequent order diffractions are either insufficiently powerful to be of relevance or are situated beyond the edges of the two gratings 14a, 14b.

Figure 13:
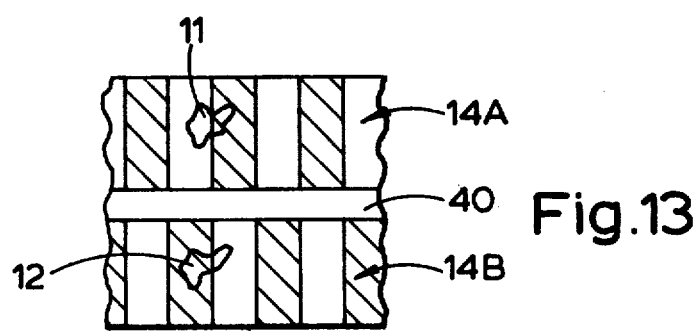
FIG. 13 is a diagram showing the effect of an aberration on the cross section of the beams.
Figure 15:
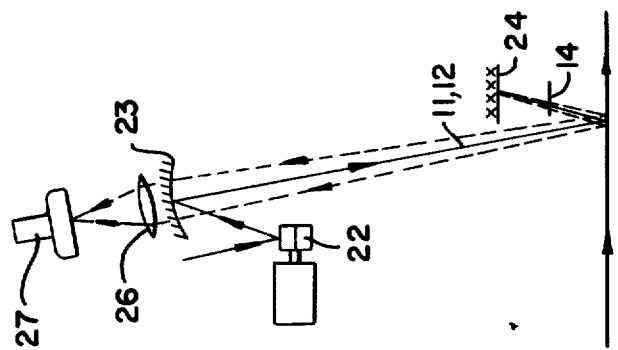
Figure 14:
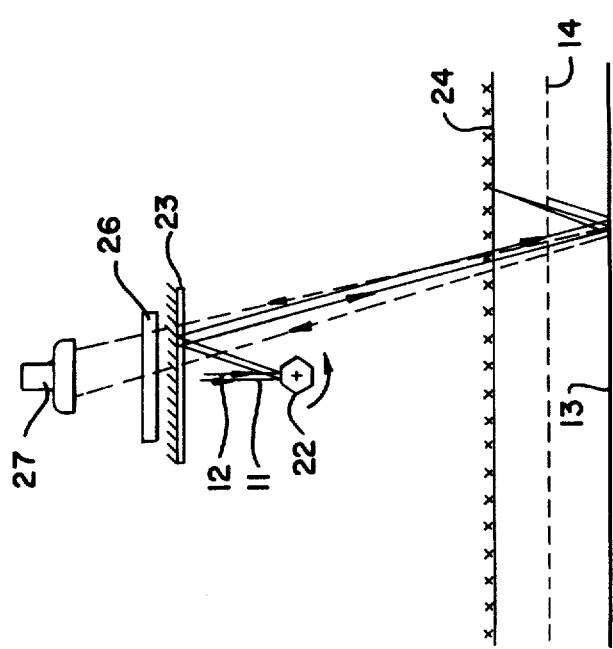

Thus any aberration produced in the laser beam before reaching the beam splitter 25 will affect equally both of the first order diffraction beams which are therefore as equal as possible. The two beams 11, 12 have the same total intensity, the same polarization angle, and the same intensity distribution within the cross-section of the beam. Thus as shown in FIG. 13 which shows the effect of aberration on the cross-section of the laser beams, even if the beams have a non-uniform intensity distribution across their cross-section, the sum of the radiation transmitted by the radiation transmitting areas 15 of the two gratings 14a, 14b, will always be constant and equal to the total intensity of either beam.

The invention is not restriction to the details of the foregoing example. It will be within the skill of a person versed in the art to devise modifications changes and improvements within the scope of the invention as set forth in the appended claims.

We claim:

1. Optical test apparatus for examining a transparent object, said apparatus comprising:
   (a) means for providing two beams of radiation,
   (b) grating means for each beam,
   (c) means for scanning each beam across the object and across its respective grating means so that each beam is passed through the object before passing to its respective grating means,
   (d) the grating means comprising first and second alternately arranged areas which influence the radiation in different ways, successive areas being of substantially the same width in the direction of scan,
   (e) the beams being displaced relative to one another and/or the grating means being displaced relative to one another by a total distance in the direction of scan equal to an odd number of widths so that, at all times during the scan, in the absence of faults in said object, one of the beams is being influenced by an area of the first type and the other of the beams is being influenced by an area of the second type, and
   (f) collector means for collecting the beams of radiation after they have been influenced by both grating means and the object.

2. Optical test apparatus as claimed in claim 1 in which the alternate areas of the grating means comprise radiation absorbing and radiation transmitting areas.

3. Optical test apparatus as claimed in claim 1 in which the alternate areas of the grating means comprise radiation transmitting and radiation reflecting areas.

4. Optical test apparatus as claimed in claim 1 in which the collector means is arranged to collect radiation passing through the grating.

5. Optical test apparatus as claimed in claim 1 in which reflective, diffuse or retro-reflective means is provided behind the grating means to reflect radiation back through the grating means and means is provided to separate the incident radiation from the reflected radiation.

6. Optical test apparatus as claimed in claim 1 in which the alternate areas of the grating means comprise radiation absorbing and radiation reflecting areas.

7. Optical test apparatus as claimed in claim 1 in which the respective grating means for each beam are provided by a single grating in phase with one another.

8. Optical test apparatus as claimed in claim 1 in which the respective grating means for each beam are provided by two gratings in phase with one another.

9. Optical test apparatus as claimed in claim 1 in which the respective grating means for each beam are provided by two gratings out of phase with another by a distance equalling the width or a multiple thereof.

10. Optical test apparatus as claimed in claim 1 wherein the radiation providing means comprises a laser.

11. Optical test apparatus as claimed in claim 1 in which the means for providing two beams of radiation comprises a beam splitter comprising a grating, the grating lines of which extend parallel to the lines of scan, the two beams of radiation being provided by first order diffraction.

12. A method of examining a transparent object comprising:
   (a) scanning two beams of radiation across the object and across respective grating means so that each beam is is passed through the object before passing to its respective grating means,
   (b) each grating means comprising first and second alternately arranged areas which influence the radiation in different ways, successive areas being of substantially the same width in the direction of scan,
   (c) the beams being displaced relative to one another and/or the grating means being displaced relative to one another by a total distance in the direction of scan equal to an odd number of widths so that, at all times during the scan, in the absence of faults in said object, one of the beams is being influenced by an area of the first type and the other of the beams is being influenced by an area of the second type and
   (d) collecting and the radiation influenced by both the grating means and the object.

13. A method as claimed in claim 12 in which the two beams of radiation are provided by first order diffraction of an incident beam of radiation.

14. Optical test apparatus for examining a reflective object, said apparatus comprising:
   (a) means for provicing two beams of radiation,
   (b) grating means for each beam,
   (c) means for scanning each beam across the object and across its respective grating means so that each beam is reflected from the object before being passed to the grating means,
   (d) the grating means comprising first and second alternately arranged areas which influence the radiation in different ways, successive areas being of substantially the same width in the direction of scan,
   (e) the beams being displaced relative to one another and/or the grating means being displaced relative to one another by a total distance in the direction of scan equal to an odd number of widths so that, at all times during the scan, in the absence of faults in said object, one of the beams is being influenced by an area of the first type and the other of the beams is being influenced by an area of the second type, and
   (f) collector means for collecting the beams of radiation after they have been influenced by both grating means and the object.

15. Optical test apparatus as claimed in claim 14 wherein
   the alternate areas of the grating means comprise radiation absorbing and radiation transmitting areas.

16. Optical test apparatus as claimed in claim 14 wherein
   the alternate areas of the grating means comprise radiation transmitting and radiation reflecting areas.

17. Optical test apparatus as claimed in claim 14 wherein
   the collector means is arranged to collect radiation passing through the grating.

18. Optical test apparatus as claimed in claim 14 wherein
   reflective, diffuse or retro-reflective means is provided behind the grating means to reflect radiation back through the grating means and means is provided to separate the incident radiation from the reflected radiation.

19. Optical test apparatus as claimed in claim 14 wherein
the alternate areas of the grating means comprise radiation reflecting areas.

20. Optical test apparatus as claimed in claim 14 wherein
the respective grating means for each beam are provided by a single grating in phase with one another.

21. Optical test apparatus as claimed in claim 14 wherein
the respective grating means for each beam are provided by two gratings in phase with one another.

22. Optical test apparatus as claimed in claim 14 wherein
the respective grating means for each beam are provided by two gratings out of phase with one another by a distance equalling the width or a multiple thereof.

23. Optical test apparatus as claimed in claim 14 wherein
the radiation providing means comprises a laser.

24. A method of examining a reflective object comprising:
(a) scanning two beams of radiation across the object and across respective grating means so that each beam is reflected from the object before being passed to its respective grating means,
(b) each grating means comprising first and second altrenately arranged areas which influence the radiation in different ways, successive areas being of substantially the same width in the direction of scan,
(c) the beams being displaced relative to one another and/or the grating means being displaced realtive to one another by a total distance in the direction of scan equal to an odd number of widths so that, at all times during the scan, in the absence of faults in said object, one of the beams is being influenced by an area of the first type and the other of the beams is being influenced by an area of the second type and
(d) collecting and analyzing the radiation influenced by both the grating means and the object.

25. A method as claimed in claim 24 wherein
the two beams of radiation are provided by first order diffraction of an incident beam of radiation.

* * * * *